United States Patent
O'Dwyer et al.

[19]

[11] Patent Number: 6,006,591

[45] Date of Patent: Dec. 28, 1999

[54] VOLATIZATION DEVICE FOR LIQUIDS

[76] Inventors: Barry O'Dwyer, 1 Meadow Road, Marlborough, N.H. 05353; Christopher D. Prozzo, RR 3, Box 169J, Athens, Vt. 05143

[21] Appl. No.: 09/015,601

[22] Filed: Jan. 30, 1998

[51] Int. Cl.[6] .................................................. G01N 1/00
[52] U.S. Cl. ...................................... 73/64.56; 73/864.81
[58] Field of Search .............................. 73/53.05, 61.41, 73/61.48, 61.55, 64.56, 863.23, 863.43, 864.21, 864.81; 239/338, 340, 373; 96/105

*Primary Examiner*—Michael Brock
*Attorney, Agent, or Firm*—Herbert M. Wolfson

[57] ABSTRACT

Apparatus and process are disclosed for transforming a liquid sample in a pressurized container to a vapor phase sample which includes the combination of a coarse filter, a flow restricting orifice, a pressure cut-off switch, a coalescing filter, and a fitting for linking the device to an analytical device.

1 Claim, 1 Drawing Sheet

VOLATIZATION DEVICE FOR LIQUIDS

BACKGROUND OF THE INVENTION

There is a continuing need to analyze containers of volatile mixtures, such as mixtures of fluorocarbon liquids and other lower boiling organic gas mixtures. The concentration of the components in the vapor space above such liquids does not correspond to the concentration in the liquid state due to several reasons. One factor is due to Raoults Law which states that the vapor concentration of a component depends upon the molefraction of that component in the liquid states. A second factor is that the vapor represents a distillation of the components in the liquid state, and many times the distillation will represent an azeotropic distillation in which the concentration of components in the liquid will control the concentration in the vapor state. It is also true that layering can occur of components in the vapor state due to differing densities in the several gases.

Other methods of achieving a gas whose composition is equal to that of the liquid in a container of volatile liquids is the evaporation of a quantity of the material which requires heat and gives a gas of uncertain pressure values, is more difficult to carry out in a precise fashion and obtain correct analytical results, nor does such a method remove the oil which will be present in a quantitative fashion.

The invention described below precludes these sorts of complexities and gives every time an analysis of the liquid state which is not skewed by any known factors on a gas at a known pressure.

SUMMARY OF THE INVENTION

The device of this invention is comprised of a number of components connected in series, the purpose being to transform a liquid sample under pressure in the liquid container into an oil and particulate free gas sample at a predetermined known pressure. The components are sequentially:

1. a 45 degree quick coupler which attaches to the liquid part of the container;
2. a 20–50 micron sintered filter which removes relatively large inert particles;
3. a small orifice 0.001" which governs the free expansion of the liquid to a gas of identical composition. At the same time the gas is generated from the liquid sample, the two oils usually present in such containers are converted into non-volatile droplets. The driving force in this evaporation is the pressure in the initial liquid container, amounting to at least 50 psi.
4. Immediately following the gas expansion orifice there is a pressure negative shut off set at 15 psi which will yield a steady flow of the gas to be analyzed through the gas cell contained in the IR filter spectrometer where the analysis is carried out;
5. In the next stage of the device there is a disposable coalescing filter which removes the oil droplets from the gas streamed. Herein contained in the filter is an oil saturation color detector which is a dye. The development of a red color indicates the filter has exhausted its capacity and should be replaced. A view port is present in this section of the device to make for ease of determination of the filter status; and
6. The final section is a SAE 45 degree fitting which is utilized to attach the volatilization device to the IR filter spectrometer employed for the analysis of the gas.

The device can be cleansed of all gases and be at ready to perform the next analysis by passing clean air through the device.

Due to the fact that air is present as a component in the liquid phase of the fluorocarbon gas mixtures, this is taken into account in the analysis performed by the filter spectrometer and expressed as a component of the mixture.

DETAILED DESCRIPTION OF THE INVENTION

Figure 1:
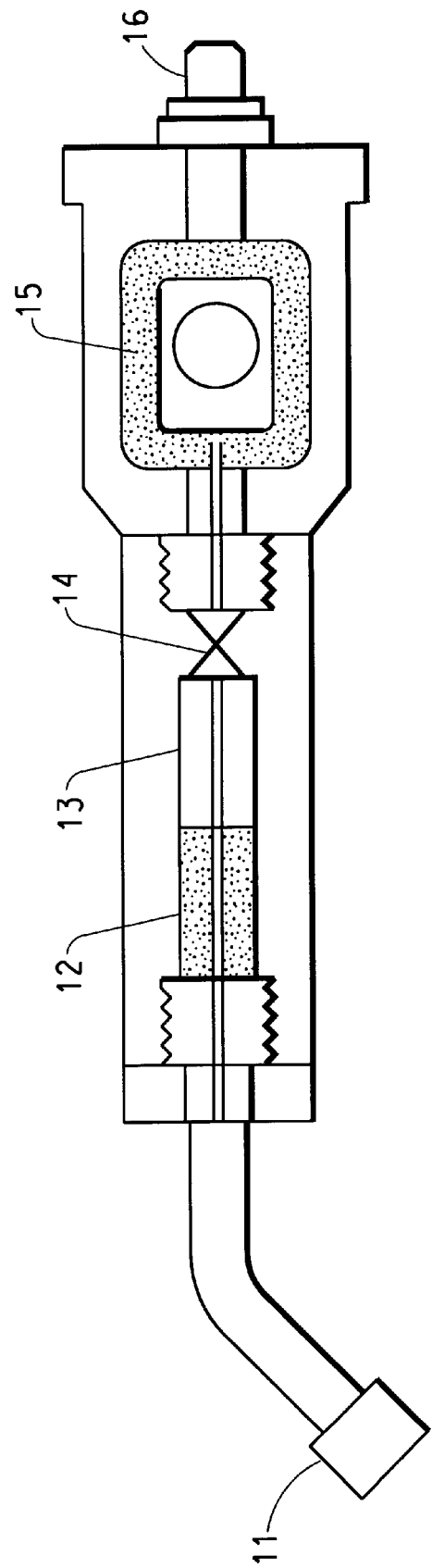
FIG. 1 is a schematic cross-sectional side view of the apparatus of the invention.

FIG. 1 designates the critical components of the device to transform a volatile liquid sample to a gas sample of identical composition.

Commonly, such a device would be useful for the analysis of pressurized containers of fluorocarbon liquids, but also applicable to other simple or complex volatile liquid compositions.

In FIG. 1, "1" designates the quick coupler which connects the vaporization device to the pressurized fluorocarbon liquid container, "2" indicates the sintered filter which is included to remove coarse particles from the liquid stream, prior to the small orifice "3". The flow restricting orifice "3" causes the free expansion of the liquid fluorocarbon which is under pressure, to yield a single or multi-component gas.

In this section of the device is a pressure regulator switch "4", with negative shutoff to give a stream of gas at a standard pressure, suitable for filling the gas cell of an attached IR gas analyzer.

The penultimate component of the volatilization device is a disposable coalescing filter to remove aerosols of any oils or non-volatile components in the original liquid contained in the pressurized container.

The final component is a suitable connector "6" to accomplish connection to the IR gas analyzer used to furnish an analysis of the gas mixture.

Alternatively, the flow restricting orifice can be replaced by a section of capillary tubing (not shown in drawing). Also, the flow restricting orifice dimension can be optimized with respect to the vapor pressure of investigated liquid sample.

We claim:

1. A device for transforming a liquid phase sample in a pressurized container of a singular component or multiple components to a heterogeneous vapor phase sample which accurately represents the molar concentration of the liquid phase sample, comprising:
   a) a connector to link said device to the liquid phase of the liquid container;
   b) a coarse filter, 20–50 microns, to remove gross particles from the liquid to be volatilized;
   c) a flow restricting orifice which allows for controlled expansion of the liquid phase to the gas phase;
   d) a pressure cut-off switch which regulates the pressure of the flowing gas to a suitable pressure to fill the gas cell of an attached IR gas analyzer;
   e) a disposable coalescing filter to remove any non-volatiles present in the gas stream; and
   f) a suitable fitting for linking the device for achieving vaporization of a liquid to a gas sample, into an IR analyzer equipped with a gas cell to contain said gas for analysis.

* * * * *